US005202168A

United States Patent [19]

Turner et al.

[11] Patent Number: 5,202,168

[45] Date of Patent: Apr. 13, 1993

[54] PRECISION RETRO-REFLECTIVE TARGET TAPE

[75] Inventors: Glenn V. Turner, Newport Beach; Dean N. Michael, Downey, both of Calif.

[73] Assignee: Northrop Corporation, Hawthorne, Calif.

[21] Appl. No.: 584,309

[22] Filed: Sep. 18, 1990

[51] Int. Cl.[5] .......... A61F 13/02

[52] U.S. Cl. .......... 428/40; 428/187; 428/216; 428/220; 428/480; 359/515; 359/530; 359/540; 359/546; 40/582; 40/615

[58] Field of Search .......... 428/40, 352, 187, 156, 428/332, 335, 220, 480, 41, 42, 216; 350/104, 97; 359/530, 531, 536, 515, 540, 542, 359, 546; 40/615, 582; 33/293

[56] References Cited

U.S. PATENT DOCUMENTS

| | | | |
|---|---|---|---|
| 1,875,766 | 9/1932 | Schubert | 428/40 |
| 3,034,406 | 5/1962 | McKenzie | 359/540 |
| 3,357,106 | 12/1967 | Schneider | 33/761 |
| 3,464,883 | 9/1969 | Moline | 428/352 |
| 3,587,415 | 6/1971 | Eigenmann | 359/540 |
| 3,821,660 | 6/1974 | Shang | 372/77 |
| 3,936,567 | 2/1976 | Vesely | 428/41 |
| 3,958,891 | 5/1976 | Eigenmann | 359/536 |
| 4,334,773 | 6/1982 | Goldberg | 356/124 |
| 4,461,795 | 7/1984 | Ogawa | 428/187 |
| 4,492,465 | 1/1985 | Erdmann | 356/150 |
| 4,656,072 | 4/1987 | Coburn | 428/40 |
| 4,875,799 | 10/1989 | Harrison | 359/531 |
| 4,904,508 | 2/1990 | Madonia | 428/40 |
| 4,913,946 | 4/1990 | Sala | 428/352 |
| 5,073,005 | 12/1991 | Hubbs | 359/515 |

*Primary Examiner*—Ellis P. Robinson
*Assistant Examiner*—Nasser Ahmad
*Attorney, Agent, or Firm*—Terry J. Anderson; Robert B. Block; Karl J. Hoch, Jr.

[57] ABSTRACT

A retro-reflective target tape comprising a lower sub-laminate having an upper transparent thick mylar backing about 2 mils thick, a release sheet therebeneath and a pressure sensitive adhesive therebetween; and an upper sub-laminate having an upper light reflective sheet with a thin, transparent mylar backing about a half mil thick therebeneath and with a pressure sensitive adhesive therebetween and with pressure sensitive adhesive beneath the thin mylar backing, the upper sub-laminate being cut to form a plurality of circular reflective targets and removed from the lower sub-laminate except for the plurality of circular reflective targets, the pressure sensitive adhesive above the release sheet remaining with the thick mylar backing upon the removal of the adjacent release sheet. Also disclosed is a method of fabricating such tape.

3 Claims, 3 Drawing Sheets

PRECISION RETRO-REFLECTIVE TARGET TAPE

BACKGROUND OF THE INVENTION

1. Field of the Invention

This invention relates to a precision retro-reflective target, tape and, more particularly, to a tape with a transparent backing and precisely sized and positioned retro-reflective targets adhered thereon for use in manufacturing processes and to a method of fabricating such tape.

2. Description of the Background Art

IN the fabrication of products, in particular aircraft components, it is important to validate aligned details and moldlines to insure that the products are properly fabricated to fulfill their intended functions. One technique foe verifying proper fabrication is to use photogrammetry in a manner long employed in the field of surveying and the like. More specifically, it is a common practice to place a tape in adhesive contact onto the side of a fabricated product such as an aircraft part. Such tape is provided with targets in the form of circular dots of a precise size, spaced a precise distance from each other, and precisely located along the length of the tape. In order to insure that such targets are in their proper positions, it is necessary to first record the image of the targets upon a photogrammetric film and then make the proper measurements with the use of a monocomparator. If the sighted targets are in proper position, then the configuration of the fabricated pat to which they are adhered is proper.

In the past, spaced targets have been formed on a retro-reflective tape or sheeting which is inked over or otherwise baked in all areas other than dots to be sighted. Typical of such tape is one marketed by the 3-M Company of Minneapolis, MN under the name of #7610 Scothc ® High Gain Reflective Sheet. It has been found, however, that circular dot targets on sheeting or tape are not always equally sized nor are they always precisely positioned with respect to each other or with respect to the edge of the tape which supports them. Additionally, errors occur in the linear alignment of dot centers, particularly when the tape is aligned on a linear abutment edge of the product workpiece. Consequently the photogrammetric sightings are onto always as accurate as possible, the fault resulting from improperly sized or positioned dots and not the photogrammetric equipment. An additional inaccuracy of prior tapes results from non-transparent support tape functioning as a target backing. The non-transparency causes a "washed-out" effect upon being photographed. Yet another shortcoming of prior tapes is the inability to remove the tape from the part being sighted after use. As a result, the photogrammetric targets often remain on the aircraft and become a part of its structure.

various approaches are disclosed in the patent literature for determining the positioning of one object or part with respect to the other. For example, U.S. Pat. No. 4,492,465 relates to a retro-reflective electro-optical angle measuring system. The particular retro-reflective tape, however, is not shown. In U.S. Pat. No. 4,334,773 to Roper, an adhesive strip is employed with a back light source. This suggests limited utility. The present invention does not require a back light source, is removable from the surface being inspected and is sufficiently flexible to be used on contoured surfaces. In U.S. Pat. No. 3,357,106 to Schneider, a measuring device is disclosed for use in building and excavating. Stick on targets are used but they are not retro-reflected. Unlike the apparatus of Schneider, the present system is designed primarily for use with photogrammetry and other optical equipment. U.S. Pat. No. 3,821,660 to Sheng relates to an apparatus for irradiation of a laser cavity. No retro-reflective tape is utilized. Further, the reflective surface is onto used for inspection of the type that is contemplated herein.

As illustrated by the great number of prior patents and commercial devices and techniques, efforts are continuously being expended in an effort to improve retro-reflective targets and their methods of fabrication. Such efforts are being made to render targets more efficient, reliable, inexpensive and convenient to manufacture and use. None of these previous efforts, however, provides the benefits attendant with the present invention. Additionally , the prior patents and commercial devices and techniques do not suggest the present inventive combination of component elements and method steps arranged and configured as disclosed and claimed herein.

the present invention achieves its intended purposes, objects and advantages through an unobvious combination f component elements and method steps with the use of a minimum number of punched-in parts, at a reasonable cost to manufacture and by employing only readily available materials.

It is therefore an object of the present invention to provide a retro-selective target tape comprising a lower sub-laminate having an upper transparent thick mylar backing bout 2 mils thick, a release sheet therebeneath and a pressure sensitive adhesive therebetween; and an upper sub-laminate having an upper light reflective sheet with a thin, transparent mylar backing about a half mil thick therebeneath and with a pressure sensitive adhesive therebetween and with pressure sensitive adhesive beneath the thin mylar backing, the upper sub-laminate being cut to for ma plurality of circular reflective targets and removed from the lower sub-laminate except for the plurality of circular reflective targets, the pressure sensitive adhesive above the release sheet remaining with the thick mylar backing upon e removal of the adjacent release sheet.

It is a further object of the invention to provide a method of fabricating such tape.

It is a further object of the invention to sight targets properly sized, located and spaced along the length of a transparent tape.

It is a further object of this invention easily remove a photogrammetric tape from the object or pat being sighted.

it is a further object of this invention to improve methods of fabricating tape with target dots properly sized, located and spaced along the length of the tape.

it is a further object of this invention to manufacture aircraft and the products more accurately.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown on the attached drawings. For the purpose of summarizing the invention, the invention may be incorporated into an improved target tape comprising a lower su-laminate having an upper first backing, a release sheet therebeneath and a pressure sensitive adhesive therebetween; and an upper sub-laminate having an upper light reflective sheet with a second backing therebeneath and with a pressure sensitive adhesive therebetween and with pressure sensitive adhesive beneath the second backing, the upper sub-laminate being cut to form a plurality of circular reflective targets.

The first backing is about 2 mils thick and the second backing is mylar about a half mil thick. Both the first and second backings are transparent. The upper sub-laminate is removed from the lower sub-laminate except for the plurality of circular reflective targets. The pressure sensitive adhesive above the release sheet remains with the first backing upon the removal of the adjacent release sheet.

The invention may also be incorporated into an improved retro-reflective target tape comprising a lower sub-laminate having an upper transparent thick mylar backing about 2 mils thick, a release sheet therebeneath and a pressure sensitive adhesive therbetween; and an upper sub-laminate having an upper light reflective sheet with a thin, transparent mylar backing about a half mil thick therebeneath and with a pressure sensitive adhesive therebetween and with pressure sensitive adhesive beneath the thin mylar backing, the upper sub-laminate being cut to form a plurality of circular reflective targets and removed from the lower sub-laminate except for the plurality of circular reflective targets, the pressure sensitive adhesive above the release sheet remaining with the thick mylar baking upon the removal of the adjacent release sheet.

The invention may also be incorporated into a tape for use in photogrammetry comprising a lower, transparent backing tape with a release sheet adhesively adhered to the lower surface thereof and a plurality of circular reflective targets operatively coupled to the upper surface thereof.

Lastly, the invention may be incorporated into an improved method of fabricating a precision reflective target tape comprising the steps of: removing a release liner from a light reflective sheet and placing it in adhesive contact with a thin mylar sheet having a release sheet therebeneath and pressure sensitive adhesive therebetween to thereby form an intermediate tape; removing the release sheet from the intermediate tape and placing it in adhesive contact with a thick mylar sheet with a release sheet therebeneath and pressure sensitive adhesive therebetween to form a final tape; cutting upper portions of the final tape into circular reflective targets; removing the upper portions of the final tape which are not reflective targets; and winding the remaining final laminate on a roll. The final tape is fabricated of a wide tape with plural rows of targets and then slit into a plurality of narrower tapes, each with only one row of targets, prior to winding the remaining final tape on a take-up roll. The cutting of the upper portions into circular reflective targets is effected y movement through a cutting roller prior to slitting.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the at that the conception and the disclosed specific embodiment may be readily utilized as a basis for modifying word designing other structures for carrying out the same purpose of the present invention. It should also be realized by those skilled in the at that such equivalent constructions do not depart from the spirit and scope of the invention as set forth in the appended claims.

BRIEF DESCRIPTION OF THE E DRAWINGS

For a fuller understanding of the nature and objects of the invention, reference should be had to the following detailed description taken in conjunction with the accompanying drawings in which.

Similar reference numbers refer to similar parts throughout the several Figures.

DETAILED DESCRIPTION OF THE INVENTION

Figures 1, 2:
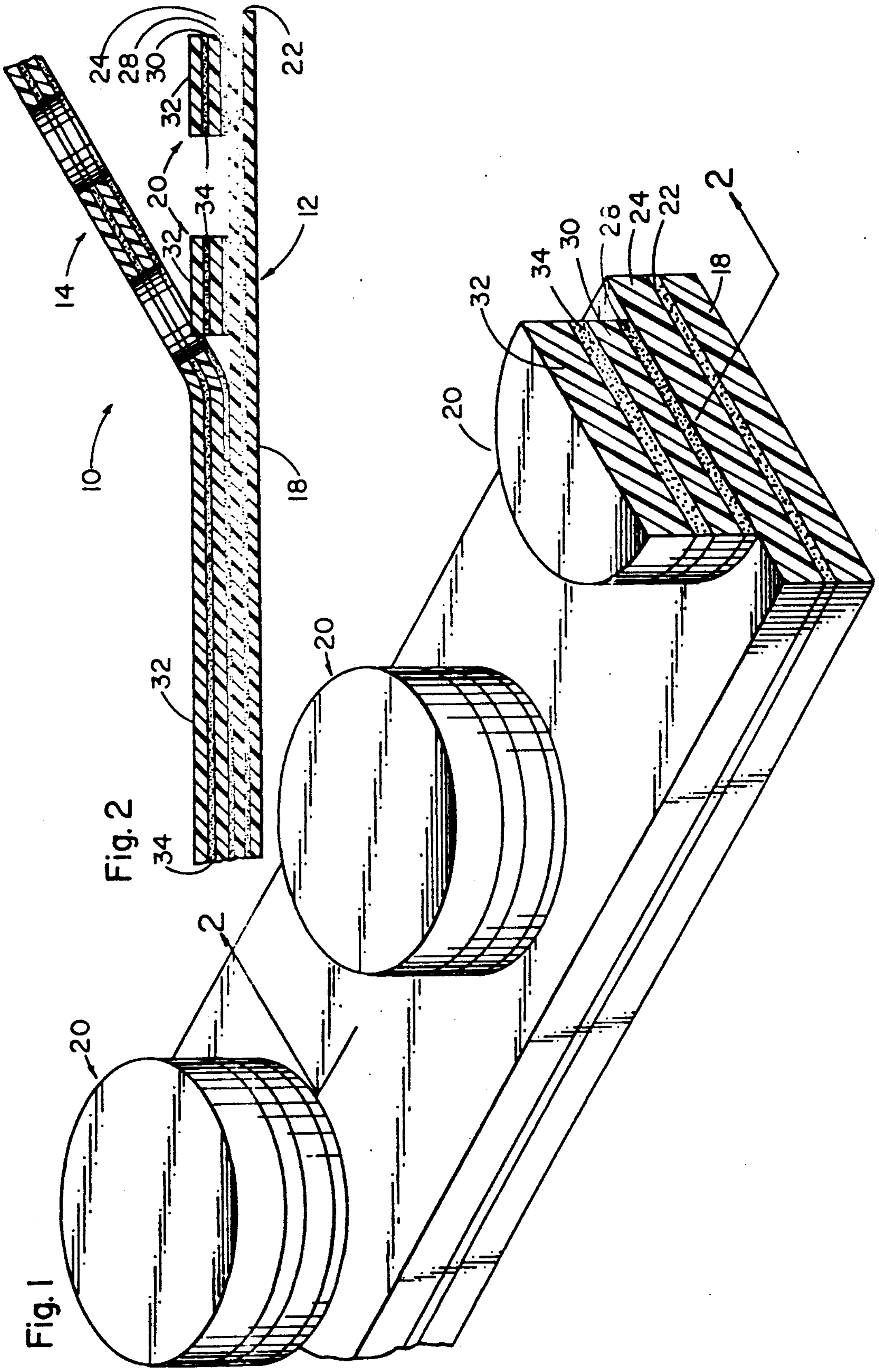
FIG. 1 is a perspective view partly in section of a photogrammetric target constructed in accordance with the principles of the present invention.
FIG. 2 is a sectional view of the tape shown in FIG. 1.

With particular reference to the Figures, there is shown in FIGS. 1 and 2 a photogrammetric tape 10 fabricated in accordance with the principles of the present invention. The tape is a multi-laser constructed of seven major component layers, three in the lower sub-laminate 12 nd four in the upper sub-laminate 14.

IN the lower sub-laminate, the lowermost layer is a lower release sheet 18. The lower release sheet is designed to be peeled away from the remainder of the laminate or tape. Once the lower release sheet is removed, the tape with targets 20 may be adhered to the product to be measured.

Nest above the lower release sheet is the lower adhesive 22 which couples the lower release sheet 18 and the layer thereabove, the thick mylar sheet 24, preferably about 2 mils in thickness. When the lower release sheet is removed, the adjacent adhesive remains solely on the thick mylar sheet so that the adjacent adhesive, thick mylar sheet and materials thereabove may be adhered to the aircraft. Together, the thick mylar sheet adjacent adhesive and lower release sheet are of an extended length along the length of the tape and constitute one of the initial inputs of the fabrication process.

Located above the thick mylar sheet 24 is the upper sub-laminate 14 which includes the plurality of spaced photogrammetric dots which function as targets 20. Each target is circular in configuration. The lowermost layer of the upper sub-laminate 14 is an intermediate adhesive 28 securing the upper surface of the thick mylar sheet to the lower surface of a thin mylar sheet 30, preferably about 0.5 mils in thickness.

Above the thin mylar sheet 3 is the 3M Schotch ® High Gain Reflective Sheeting or tape 32 which constitutes the upper, exterior surface for sighting purposes. The reflective sheet or tape 32, the upper adhesive 34, the tin mylar sheet 30 and the intermediate adhesive 28 therebeneath constitute the upper sub-laminate 14.

Both the thin and thick mylar sheets are preferably transparent to preclude a "wash-out" effect which would occur if the target tape has high gain reflective sheeting with improper inking or masking in the non-dot regions Further, since the reflective sheet is somewhat extensible, capable of being stretched, its backing sheet is preferably inextensible.

In use, the operator would simply pull from a rewind cylinder 38, the correct length of photogrammetric tape 10 and cut it for use. From one end thereof the operator would begin to remove the lower release sheet 18 thereby exposing the adhesive for coupling of the aircraft. The lower release sheet 18 would then continue to be pulled off while the lower adhesive 22 and parts thereabove were adhered to the aircraft. When the lower release sheet 18 is totally removed, and with the remaining components of the tape thereabove being totally secured to the aircraft, the measurement could be properly performed. After use, the entire materials, adhesives included, may be readily removed from the aircraft by simply peeling.

Figure 3:
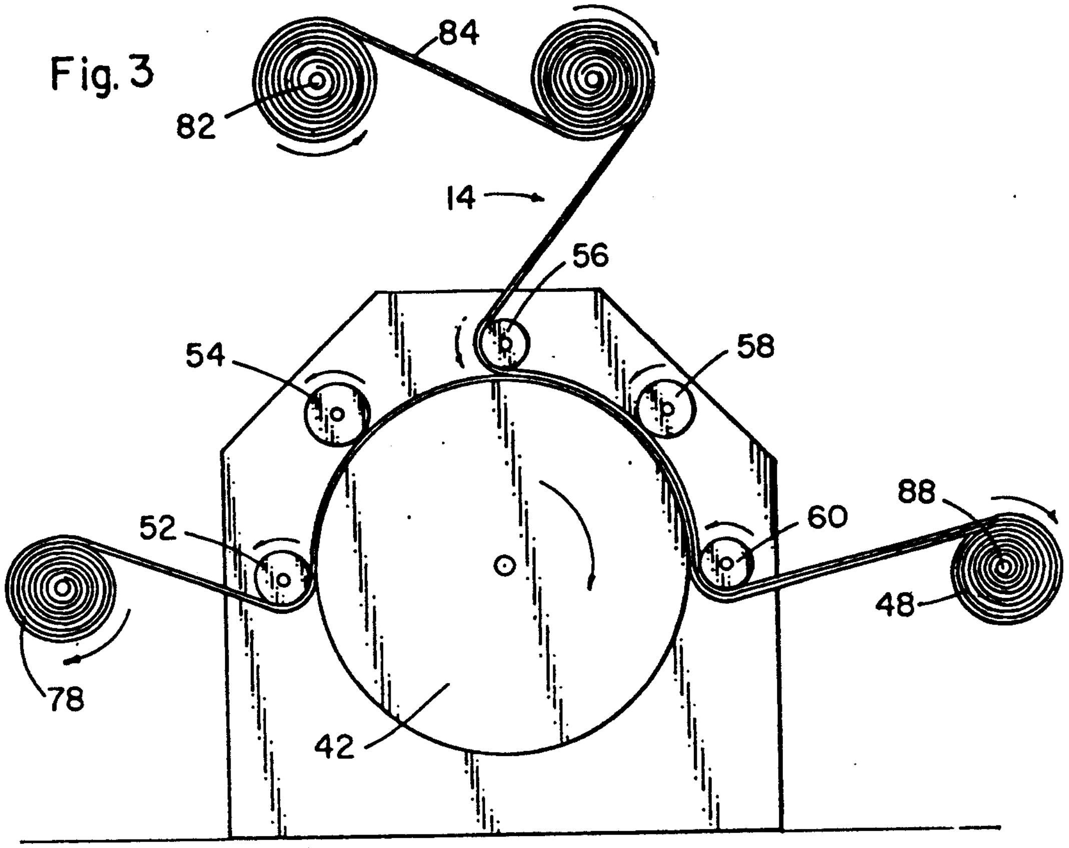
FIGS. 3 and 4 are sectional views of apparatus for fabricating the tape as shown in FIG. 1.
Figure 4:
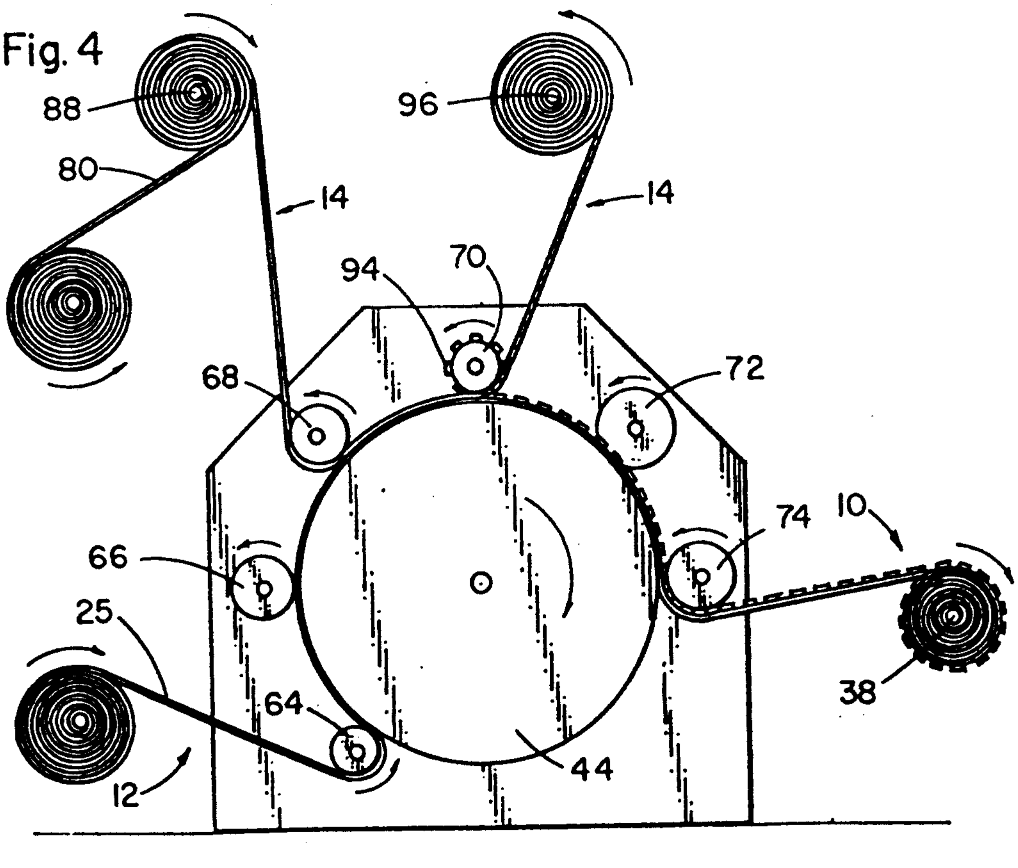

FIGS. 3 and 4 are schematic illustrations of rotary presses 42 and 44 and input component material as well as output component material to illustrate the fabrication process for the tape of the present invention. FIG. 3 illustrates the first step of the process. FIG. 4 illustrates the second step. The two steps may be done sequentially on adjacent machines in a continuous and automatic cycle of operation without intermediate rewinding as illustrated by FIGS. 3 and 4. In such case, the intermediate laminate 48 which is formed on the press of FIG. 3 would be fed directly as one of the inputs to the press of FIG. 4 with the intermediate or output tape of FIG. 3 being the input of the second rotary press on the two step poses. It should also be understood that a single rotary press could be used for both h first and second steps. In such a case the output tape of the first step would be rewound as an input for the rotary press in the second step.

The rotary presses 42 and 44 of the first and second steps are substantially identical in construction and include any large primary cylinder with a plurality of smaller idler rolls 52, 54, 56, 58 and 60 as well as 64, 66, 68 and 74 spaced around the periphery of retaining the sheet material is contact therewith. IN the first step of fabricating the target tape, the thin mylar laminate 78 is fed into contact with the rotary press 42. A first idler roll 52 insures proper direction and positioning. The tin mylar laminate 78 is comprised of the thin mylar sheet 30 with intermediate adhesive 28 and a backing material 80. This input is located at approximately the 9 o'clock position. At the 12 o'clock position is the 190,200 laminate of 3M #7610 Scotch ® High Gain Reflective Sheeting or tape 32, upper adhesive 34 and its backing. Such Reflective sheeting is fed to the rotary press 42 y being passed around an idler roll 56 before placing it in contact with the fed thin mylar sheet 30 with tis backing. A supplemental roll 82 is driven to take up the release sheet 84 from the reflective sheeting. The arrangement of parts and input materials results in an intermediate laminate 48 being fed to the 3 o'clock position of the main cylinder where it passes around an idler roll 60 onto a driven rewind roll 88. The output of the first step on the rewind roll is then ready for being fed as one of the two inputs to the rotary press 44 of the second step of the process of fabricating the target tape.

Figure 5:
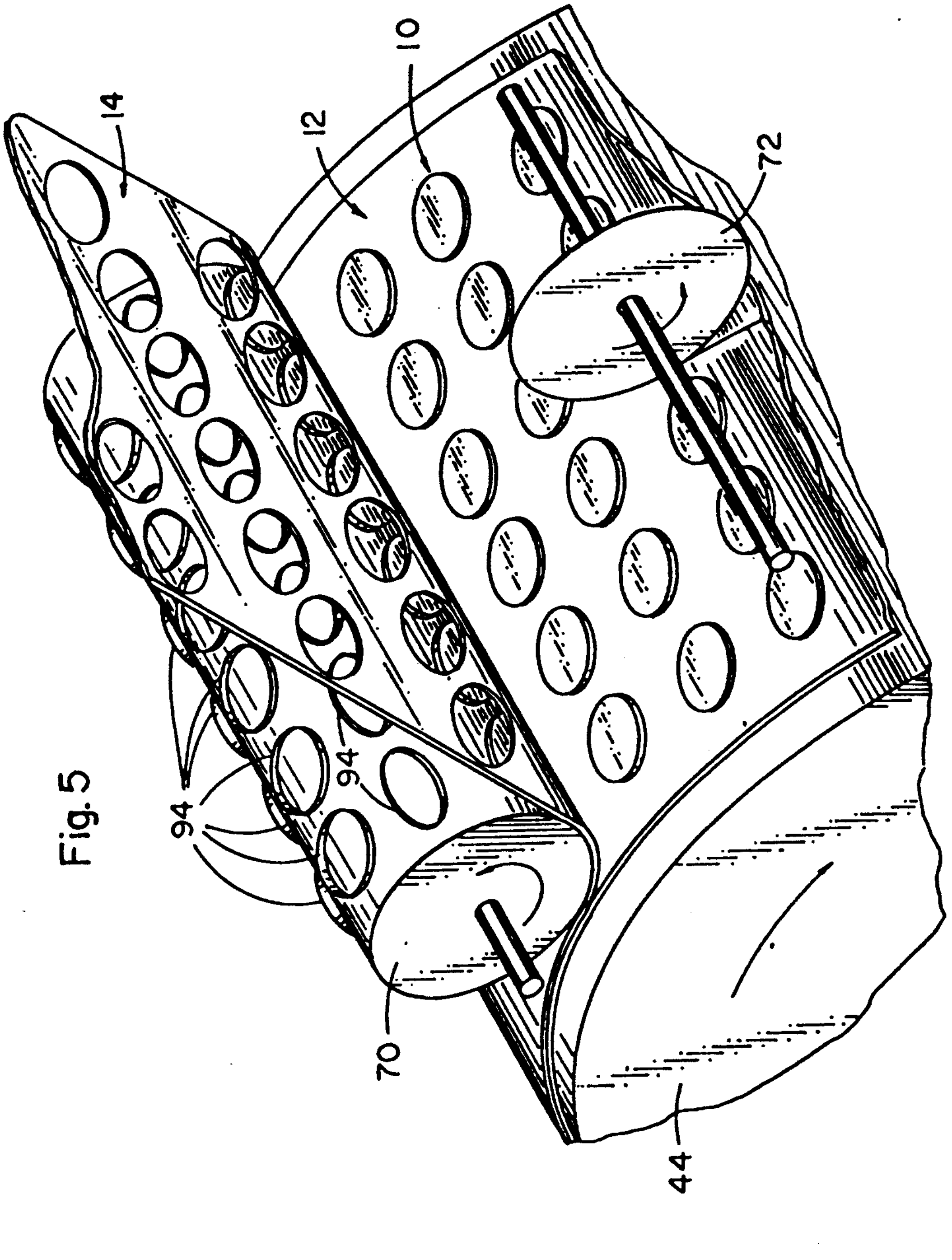
FIG. 5 is a perspective view of cutting and slitting rollers as shown in FIG. 4.

The second step of the process includes the feeding of a thick mylar laminate 245 to the second rotary press 44, being passed around an idler roll 64 at about 7 o'clock on the main cylinder. The thick mylar laminate 25 is comprised of the thick mylar sheet 24, a lower adhesive 22 and a lower release sheet 18. The thick mylar laminate 25 is then fred to about the 10O'clock position where the output of the first step, the intermediate laminate 48, is fed into contact with the thick mylar laminate 25 on the rotary press 44. A supplemental roll takes off the backing material 80 from the intermediate laminate 48 as waste.

cutting of the reflective dots from the final tape is done by a roll or cylinder 70 provided with external cutting surfaces 94 on its periphery. This occurs at about the 12 o'clock position. In addition, a second rewind waste cylinder 96 takes off those portions of the upper laminate which do to constitute the target dots of the final product. FIG. 5 is a perspective illustration of the cylinder 70. Prior to the final product being removed from the main cylinder at 3o'clock, it passes beneath a slitter roll 72 to a separate the sheet material into a plurality of strips, each having a single row of reflective target dots along its length. A driven rewind cylinder 38 makes the final winding of the end product.

The present disclosure includes that contained in the appended claims as well as that of the foregoing description. Although its invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

What is claimed is:

1. A precision retroreflective target tape for use in photogrammetric measurement of an object comprising:

a lower sub-laminate having a transparent first backing about 2 mils thick, a release sheet therebeneath and a lower pressure sensitive adhesive therebetween; and an upper sub-laminate in adhesive contact with the first backing, the upper sub-laminate having a light reflective sheet with a transparent second backing about 0.5 mils thick therebeneath and with an upper pressure sensitive adhesive therebetween and with an intermediate pressure sensitive adhesive beneath the second backing, the upper pressure sensitive adhesive tenaciously adhering the light reflective sheet to the second backing, the intermediate pressure sensitive adhesive tenaciously adhering the second backing of the first backing, the upper sub-laminate being cute to form a plurality of circular reflective targets and being removed from the lower sub-laminate except for the plurality of circular reflective targets, the lower pressure sensitive adhesive remaining with the first backing upon removal of the release sheet and having low adhesive power for removably adhering the remaining target tape to the object.

2. A precision retroreflective target tape for use in photogrammetric measurement of an object, comprising:

a transparent thick mylar sheet about 2 mils thick;

a plurality of circular reflective targets tenaciously adhered to an upper surface of the thick mylar sheet, each circular reflective target having a lightly reflective layer opposite from the thick mylar sheet, a transparent thin mylar sheet about 0.5 mils thick beneath the light reflective layer, an upper pressure sensitive adhesive layer therebetween having high adhesive power for tenaciously adhering the light reflective layer to the thin mylar sheet, and an intermediate pressure sensitive adhesive layer beneath the thin mylar sheet, the intermediate pressure sensitive adhesive layer having high adhesive power for tenaciously adhering the tin mylar sheet to the thick mylar sheet;

a lower pressure sensitive adhesive layer beneath the thick mylar sheet opposite from the circular selective targets; and, a release sheet removably adhered to the lower pressure sensitive adhesive layer opposite from the thick mylar sheet, the lower pressure sensitive adhesive layer remaining with the thick mylar sheet upon removal of the release sheet and having low adhesive power for removably adhering the thick mylar sheet and the plurality of circular reflective targets tenaciously adhered thereto to the object.

3. A precision retroreflective tape for use in photogrammetric measurement of an object, comprising a transparent first backing with a release sheet adhesively adhered to a lower surface thereof by a lower pressure sensitive adhesive nd having a plurality of circular reflective targets tenaciously adhered to an upper surface of the first backing, the lower pressure sensitive adhesive remaining with the first backing upon removal of the release sheet and having low adhesive power for removably adhering the first backing to the object, wherein each circular reflective target comprises a light reflective layer, a transparent second backing therebeneath, an upper pressure sensitive adhesive layer between the light reflective layer and the second backing, the upper pressure sensitive adhesive layer having high adhesive power for tenaciously adhering the light reflective layer to the second backing, and an intermediate pressure sensitive adhesive layer between the second backing and the first backing, the intermediate pressure sensitive adhesive layer having high adhesive power for tenaciously adhering the second backing, and the light reflective layer tenaciously adhered thereto to the first backing.

* * * * *